(12) United States Patent
Hawkins et al.

(10) Patent No.: US 9,395,390 B2
(45) Date of Patent: Jul. 19, 2016

(54) EDDY CURRENT INSPECTION PROBE

(71) Applicant: WESTINGHOUSE ELECTRIC COMPANY LLC, Cranberry Township, PA (US)

(72) Inventors: Phillip J. Hawkins, Irwin, PA (US); Lyman J. Petrosky, Latrobe, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 313 days.

(21) Appl. No.: 13/795,109

(22) Filed: Mar. 12, 2013

(65) Prior Publication Data

US 2013/0335111 A1    Dec. 19, 2013

Related U.S. Application Data (60) Provisional application No. 61/661,441, filed on Jun. 19, 2012.

(51) Int. Cl.
| | | |
|---|---|---|
| *G01R 1/067* | (2006.01) | |
| *G01M 3/00* | (2006.01) | |
| *G01N 27/90* | (2006.01) | |

(52) U.S. Cl.
CPC .............. *G01R 1/067* (2013.01); *G01M 3/005* (2013.01); *G01N 27/902* (2013.01)

(58) Field of Classification Search
CPC ..... G01N 27/82; G01N 29/04; G01N 27/902; G01N 27/9033; G01N 27/90; G01N 27/9006; G01N 27/9013; G01N 2291/2636; G01M 19/00; G01M 3/005; G03B 37/00; F16L 55/16; F16L 2101/30; G01R 1/067

USPC ......... 324/262, 238, 240, 318, 309, 209, 228, 324/219–221
See application file for complete search history.

(56) References Cited

U.S. PATENT DOCUMENTS

| | | | | |
|---|---|---|---|---|
| 4,218,923 | A * | 8/1980 | Triplett et al. | 73/623 |
| 4,249,810 | A * | 2/1981 | O'Connor et al. | 396/19 |
| 4,303,884 | A | 12/1981 | Malick | |
| 4,668,912 | A | 5/1987 | Junker | |
| 4,757,258 | A | 7/1988 | Kelly, Jr. et al. | |
| 4,842,059 | A * | 6/1989 | Tomek | 166/65.1 |
| 5,204,622 | A * | 4/1993 | McCaslin et al. | 324/220 |
| 5,254,944 | A | 10/1993 | Holmes et al. | |
| 5,565,633 | A * | 10/1996 | Wernicke | 73/865.8 |
| 5,914,595 | A * | 6/1999 | Piriou | G01N 27/9013 324/220 |

(Continued)

OTHER PUBLICATIONS

International Search Report for PCT/US2013/044872 dated Nov. 14, 2013 (Form PCT/ISA/210).

(Continued)

*Primary Examiner* — Jermele M Hollington
*Assistant Examiner* — Dustin Dickinson
(74) *Attorney, Agent, or Firm* — Joseph C. Spadacene; Westinghouse Electric Company LLC (57) ABSTRACT

A probe for transporting a nondestructive inspection sensor through a tube, that employs wheels to reduce friction. The radial travel of the wheels are mechanically linked through a cam and axially reciprocal plunger arrangement that centers the probe at tube diameter transitions. Internal wire bending is minimized and a dynamic seal is provided to facilitate an insertion force at the probe and reduce or eliminate compressive load buckling of the flexible cable carried by the probe. Like the wheel arrangement, radial travel of the seal segments are mechanically linked to provide probe centering.

19 Claims, 9 Drawing Sheets

(56) References Cited

U.S. PATENT DOCUMENTS

| | | | | |
|---|---|---|---|---|
| 5,969,275 | A * | 10/1999 | Moe | 73/866.5 |
| 6,107,795 | A * | 8/2000 | Smart | 324/220 |
| 6,820,653 | B1 * | 11/2004 | Schempf et al. | 138/98 |
| 2004/0093966 | A1 * | 5/2004 | Petit | G01N 29/22 73/866.5 |
| 2004/0112152 | A1 * | 6/2004 | Stout et al. | 73/865.8 |
| 2008/0048682 | A1 * | 2/2008 | Brusco | G01B 21/08 324/700 |
| 2010/0113942 | A1 * | 5/2010 | Eberle | 600/478 |
| 2010/0301691 | A1 * | 12/2010 | Cors et al. | 310/83 |
| 2011/0089937 | A1 * | 4/2011 | Petrosky | 324/220 |
| 2011/0125462 | A1 * | 5/2011 | Petrosky | F22B 37/003 702/188 |

OTHER PUBLICATIONS

Written Opinion of the International Searching Authority for PCT/US2013/044872 dated Nov. 14, 2013 (Form PCT/ISA/237).

International Preliminary Report on Patentability for PCT/US2013/044872 dated Dec. 31, 2014 (Forms PCT/IB/362, PCT/IB/373, PCT/ISA/237).

Westinghouse Electric Company LLC, EP 13806825.9 Search Report, Feb. 5, 2016, 7 pages.

* cited by examiner

EDDY CURRENT INSPECTION PROBE

CROSS REFERENCE TO RELATED APPLICATION

This application claims priority under 35 U.S.C. §119(e) from Provisional Application Ser. No. 61/661,441, entitled "Eddy Current Inspection Probe," filed Jun. 19, 2012.

BACKGROUND

1. Field

This invention pertains generally to the nondestructive examination of tubular specimens and, more particularly, to an inspection probe for the nondestructive examination of the structural integrity of heat exchanger tubing.

2. Related Art

In pressurized water reactor nuclear power plants, steam generators convert the thermal energy of water from the reactor coolant to steam to drive turbine electric generators. In order to transfer the heat while maintaining separation between the high pressure water that flows through the reactor core and the lower pressure water that is converted to steam, steam generators are constructed of thousands of small diameter tubes which provide a large surface area for heat transfer. The number of tubes in a steam generator range from about 3,000 to 15,000. Some steam generators utilize straight length tubes each about 60 feet long. Most of the steam generators are constructed of U-shaped tubing or long vertical sections with two 90° bends joined by a shorter horizontal length of tubing. During plant operation, the high pressure water that flows through the reactor core transports some amount of radioactive particles through the steam generators and some particles become deposited on the interior surface of the tubes. After plant operation, the steam generators become a source of radiation.

Periodic inspection with eddy current probes is widely utilized to ensure the structural integrity of steam generator tubing. Due to the elevated radiation fields, robotics and remote controlled motorized devices are used to position and translate eddy current probes. The cost of equipment, labor, plant down time, and the benefit of minimizing personnel radiation exposure make it highly desirable to optimize the performance and capability of eddy current inspection probes.

One problem with the prior art eddy current probes is that a single probe does not access all the tubes in a steam generator. The larger diameter probes used to inspect the majority of the tubes will not pass through the small radius bends in the tubing. To access the small radius bends, a small probe with less resolution may be used. Additionally, in order to inspect the entire tube, only one half of the tube may be accessed from one side of the steam generator and the second half of the tube may require access from the opposite end of the tube. To maximize productivity, this usually requires the use and disposal of additional probes.

A second problem with current eddy current probes is the probe centering mechanism. Typically, the probes are centered employing compliant pads that extend out radially at equally spaced circumferential locations around the probe. The relatively small surface area of contact between the probes and tube increases radial material loss due to wear. To compensate for wear, the pads are slightly oversized which increases friction between the tube and the pads. A further drawback of the probe centering pads is that each pad is compressed, the amount of deflection is independent from one pad to another pad. Side loads developed as the probe traverses bends in the tubing can adversely impact the centering of the probe. Additionally, the axial location of probe centering pads relative to the probe inspection coil can cause the coil to contact the tube surface as the probe traverses bends, which can adversely affect proper interpretation of the sensor signals.

Another problem currently experienced is probe electrical signal failures. While the cause of electrical failures can be ambiguous, controlling the amount of flexure of the probe is expected to decrease stress in the probe wiring and reduce electrical failures.

An additional difficulty currently encountered during eddy current inspection is in regard to inserting the probe into the tube. Typically, an eddy current probe is pushed into the tube by mechanical means such as wheels or belts which engage the probe's flexible cable. Probe friction with the tube, gravity, and rubbing of the flexible cable attached to the probe induce forces that oppose insertion of the probe. The flexible cable attached to the probe tends to buckle and the side loads imparted on the tube further increase the friction force opposing insertion. In many cases, the friction due to buckling will continue to increase the buckling load and further increase friction until it is not possible to insert the probe regardless of the force applied. Since the probe position is measured externally by encoding the flexible cable displacement, buckling of the flexible cable also causes loss of probe position accuracy.

As previously described, there are a number of problem areas with current eddy current inspection techniques. It is an object of this invention to provide a single eddy current probe to access the entire steam generator tubing including the smallest radius U-bends.

It is a further object of this invention to provide such a probe that has wheels to reduce friction in all areas of the tube including the point of insertion, diameter transitions, dents and bends.

It is an additional object of this invention to provide such a probe that will keep the sensor centered through diameter transitions, bends and other anomalies in the tube.

It is a further object of this invention to provide such an inspection probe that limits internal wire bending to enhance probe life.

It is an additional object of this invention to provide such a probe that has a dynamic seal that will enable an insertion force at the probe and move the probe along while maintaining it centered.

Additionally, it is an object of this invention to provide such a probe that has enhanced axial position accuracy.

SUMMARY

These and other objects are achieved by an elongated nondestructive sensor inspection probe having a central axis running along the elongated dimension of the probe, for nondestructively examining the walls of tubing. The inspection probe includes a nose section having at least three sets of rollers substantially equidistantly spaced around a circumference of the nose section, the sets of rollers being biased in a radially outward direction to contact an interior wall of the tubing with a substantially equally applied force biasing each of the sets of rollers. A nondestructive sensor section is suspended at one axial end from the nose section and coupled to the nose section with a pivot coupling that enables the nondestructive sensor section a limited degree of rotation relative to the nose section. A tail section is coupled to the nondestructive sensor section at another axial end with a pivot coupling that enables the nondestructive sensor section a limited degree of rotation relative to the tail section. The tail section has a centering device biased radially outward from a central body of the tail section. The centering device has a plurality of contact points with the interior wall of the tubing with each of the contact points being biased outward around the circumference of the tail section, with substantially equal pressure.

In one embodiment, the nose section includes a plunger reciprocally moveable in the axial direction, a cam coupled between each of the rollers and the plunger and means for biasing the plunger in one direction that rotates each cam to bias the rollers radially outward with substantially equal force. Preferably, the plunger is coaxially supported within the nose section and the plunger is spring biased. The tail section may similarly include a plunger reciprocally moveable in the axial direction, a cam coupled between each of the contact points and the plunger and means for biasing the plunger in one direction that rotates each cam to bias the contacts radially outward with substantially equal force. In one embodiment, the plunger in the tail section includes an axial passage through which a signal cable extends from the nondestructive sensor section to a rear of the tail section. In the latter embodiment, preferably the pivot coupling between the tail section and the nondestructive sensor section includes an axial passage through which the signal cable passes from the nondestructive sensor section to the tail section.

In another embodiment, the contact points are rollers that are substantially equidistantly spaced around a circumference of the tail section. In another embodiment, the contact points are sections of an annular circumferential seal that extend around and project outwardly from a central body of the tail section and are biased against the interior wall of the tubing. In the latter embodiment, preferably the sections of the annular circumferential seal overlap circumferentially to accommodate varying diameters of the tubing. In the latter embodiment, the sections of the annular circumferential seal may include a fluid path extending from the rear of the tail section to a radially facing interior surface of the sections of the annular circumferential seal so that a pressure buildup to the rear of the tail section forces the seal in a radially outward direction.

Generally, the nondestructive sensor section of the nondestructive sensor inspection probe of this invention is supported substantially equidistantly spaced around the circumference of the nondestructive sensor section from the pipe wall as the nondestructive sensor inspection probe traverses a bend in the pipe. Preferably, the equidistance spacing around the circumference of the nondestructive sensor section from the interior wall of the pipe does not vary substantially more than from +20% to −20% of the nominal spacing.

In still another embodiment, each set of rollers includes two rollers that move radially together. Additionally, in one given embodiment, a stop is provided for limiting the degree of rotation of the pivot coupling between the nondestructive sensor section and the tail section. Preferably, the stop limits rotation of the pivot coupling between the nondestructive sensor section and the tail section by preventing axial rotation of the tail section relative to the nondestructive sensor section.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENT

Figure 1A:
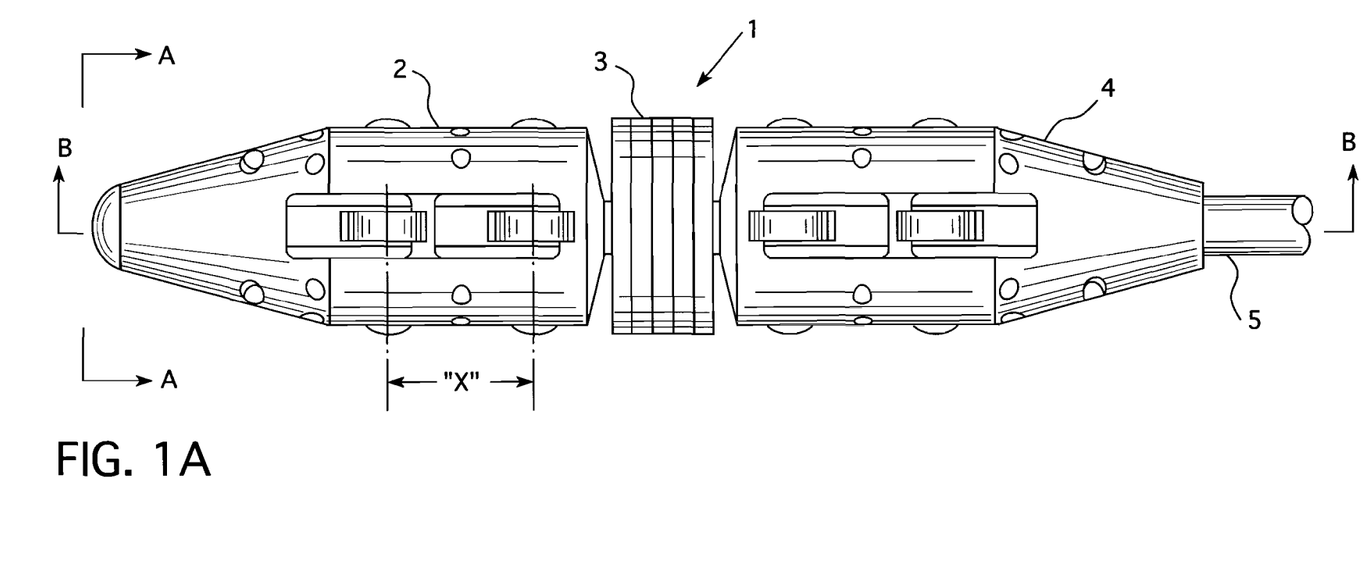
FIG. 1a is a plan view of an eddy current inspection sensor incorporating the principles of one embodiment of this invention.

FIG. 1a shows a plan view of an eddy current probe assembly 1 that incorporates the principles of this invention though it should be appreciated that a probe assembly incorporating these principles can employ any one of a number of nondestructive sensors and should not be limited to just the use of an eddy current probe. The three main parts of the probe assembly 1 are the nose assembly 2, coil assembly 3 and tail assembly 4. Flexible cable 5 is used to translate the probe assembly 1 along the interior of the tube.

Figure 1B:
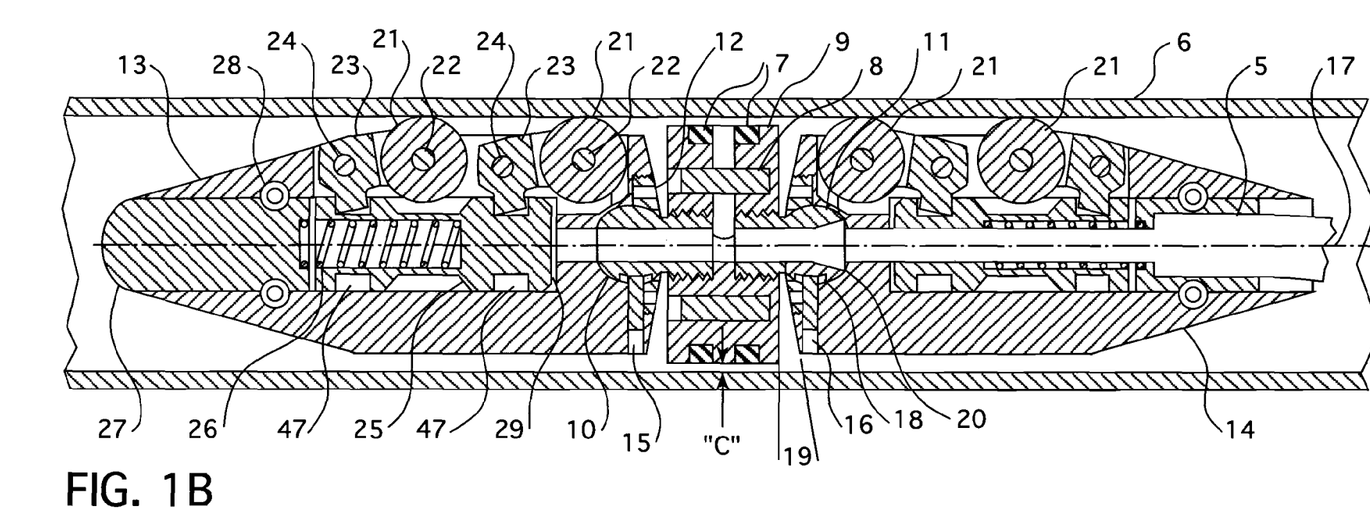
FIG. 1b is a cross sectional view of the sensor shown in FIG. 1a taken along the lines B-B thereof, positioned within a tube to be inspected.

FIG. 1b shows a cross sectional view of the probe assembly 1 shown in FIG. 1a with section B-B taken through the center of the probe assembly, positioned within a tube 6 to be inspected. While various coil configurations are used in eddy current probes, a typical bobbin probe configuration is shown with circumferential coils 7 along with permanent magnet 8 fixed by means of coil support 9. Unique to this invention is the means to position the coils 7 relative to the tube 6 as the probe is translated along the axis of the tube. It is also highly desirable to maintain an equidistant radial gap ("c") between the coils 7 and the tube 6.

Maintaining the equidistant gap is a greater challenge as the probe translates through curved sections of tubing. The function of the tail assembly 4 and moreover the nose assembly 2 is to maintain the probe centered in the tube 6. This is for both to provide a more accurate eddy current signal and to avoid contact resulting in friction and wear between the coil 7 and the tube 6.

The coil assembly 3 is coupled to the nose assembly 2 and tail assembly 4 with pivot couplings with spherical ended shafts 10 and 11 which thread into the coil support 9. The threaded retainers 12 provide the means to couple each spherical shaft to the corresponding nose body 13 or tail body 14. A small amount of clearance between each spherical shaft and a corresponding spherical recess or socket in the retainer 12 and body 13, 14 permits spherical translation between the coil assembly 3 and the nose/tail assemblies 2, 4. As will be shown later, the axial locations of the spherical centers provides probe centering as the probe translate through bends in the tubing. Pins 15 and 16 provide two functions. After retainer 12 are threaded in place, the pins prevent the retainers from unthreading. Pins 15 and 16 can also be used to provide a fixed radial orientation between the tail body 14 and the coil support 9 about the probe axis 17. This is important as not to twist the wiring between cable 5 and coil 7. As shown in the tail assembly 4, pin 16 is partially engaged into a circular slot 18 in the spherical shaft 11 which maintains radial orientation between the tail assembly 4 and the coil assembly 3.

To negotiate bends in the tubing 6, the nose assembly 2, coil assembly 3 and tail assembly 4 can rotate up to the angle 19. Rotation beyond angle 19 is prohibited as contact is made between the coil support 9 and the tail body 14. The angle 19 limits the bending stress applied to the wiring within the probe tail to coil joint. Present eddy current designs have flexible connections which may not prohibit excessive stress on the internal wiring leading to probe failure. Tapered opening 20 in the wiring exit from the pivot coupling to the tail section assembly 4 permits spherical shaft 11 to rotate without impinging on wires located within.

Since there is no wiring in the nose assembly 2, the orientation function of pin 15 is not necessarily required but desire to maintain alignment of the nose and tail for the probe type shown. For some types of eddy current probes, it is desirable to have different configurations of coils 7 that rotate about probe axis 17 as the probe is translated along the tube axis. In this case, pin 15 would not be engaged in the spherical shaft 10. Rotational compliance between spherical shaft 10 and nose body 13 permits rotation of coil assembly 3 relative to nose body 2 and tube 6.

Figure 1C:
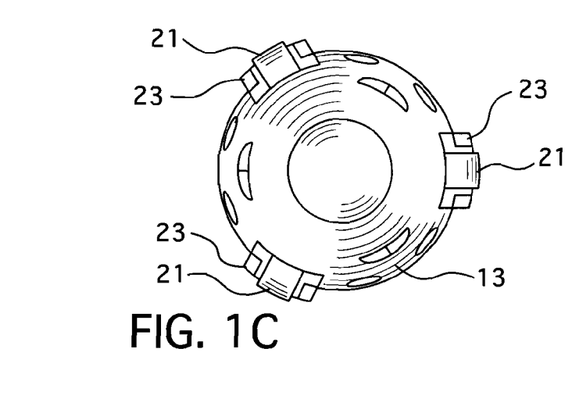
FIG. 1c is a frontal view of FIG. 1a taken along the lines A-A thereof.

Both the nose assembly and tail assembly contain wheels 21 that contact and provide a rolling coupling between the probe assembly and the tube 6. FIG. 1c shows a front view A-A of the nose assembly 2 with at least three sets of wheels 21 needed to provide centering of the probe. As shown in FIG. 1b, the wheel arrangement is very similar in the nose assembly 2 and tail assembly 4. Referring to the nose assembly 2 of the probe, wheels 21 rotate about axles 22 which are fixed to cams 23. Wheel pairs are separated by distance "X". The cams 23 are free to rotate about pins 24 that are fixed to the nose body 13. Each cam 23 is engaged into opening 47 of plunger 25. Plunger 25 is free to slide co-linearly along the axis of the nose body 13 and is biased to the right by means of compression spring 26. The reaction force of spring 26 is to the cap 27 then through spring pins 28 back to the nose body 13. As can be seen, the radial motion of each wheel toward the tube 6 is closely coupled by means of cams 23 and plunger 25. All six wheels travel the same radial distance outward with the same pressure. This feature maintains the nose body 13 equidistance from the tube 6 inside surface and wheel separation ("X") forces the axis of the nose body co-linear with the axis of the tube. When the probe is outside the tube, it is desirable to limit the maximum outward radial travel of the wheels. The travel is limited by the gap 29 between the plunger 25 and the nose body 13. The configuration is very compact as the inside diameter of tubing can be quite small.

Figure 2A:
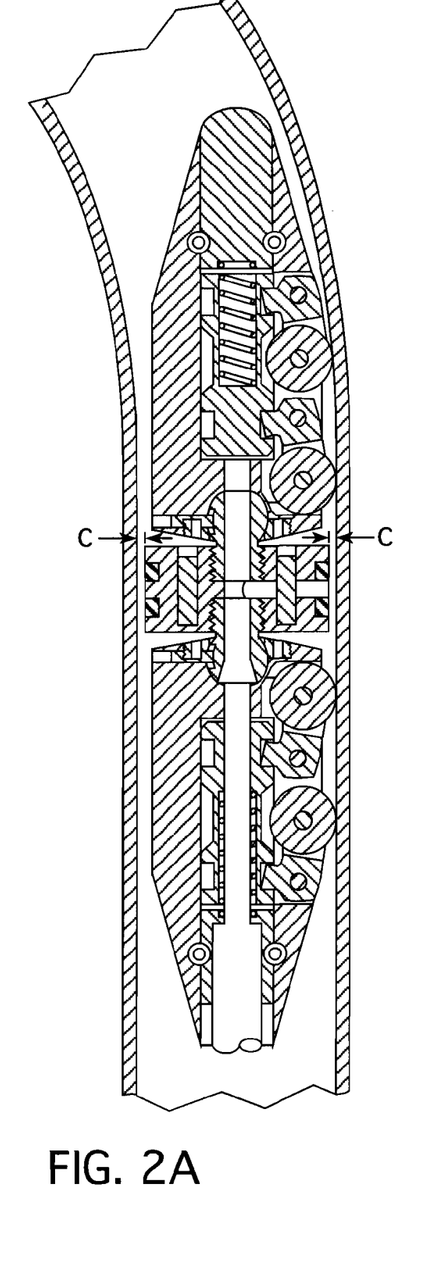
FIGS. 2a-2e are cross sectional views of the sensor embodiment illustrated in FIG. 1a positioned in a pipe to be inspected starting with FIG. 2a with the sensor positioned just at a U-bend with the sensor gradually moved around the U-bend as shown in FIGS. 2b-2e.
Figure 2B:
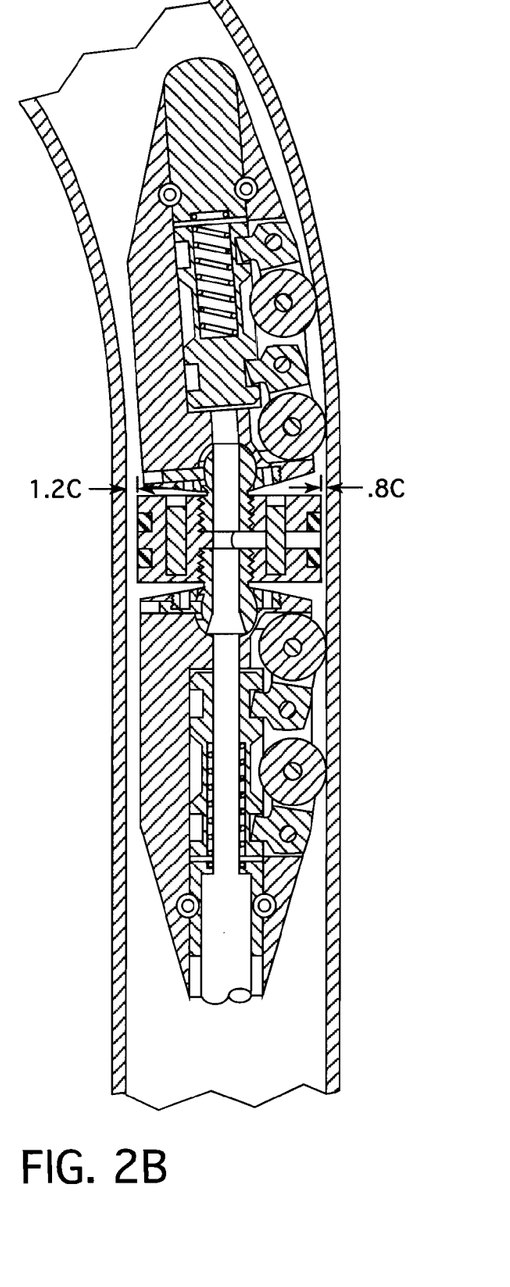
Figure 2C:
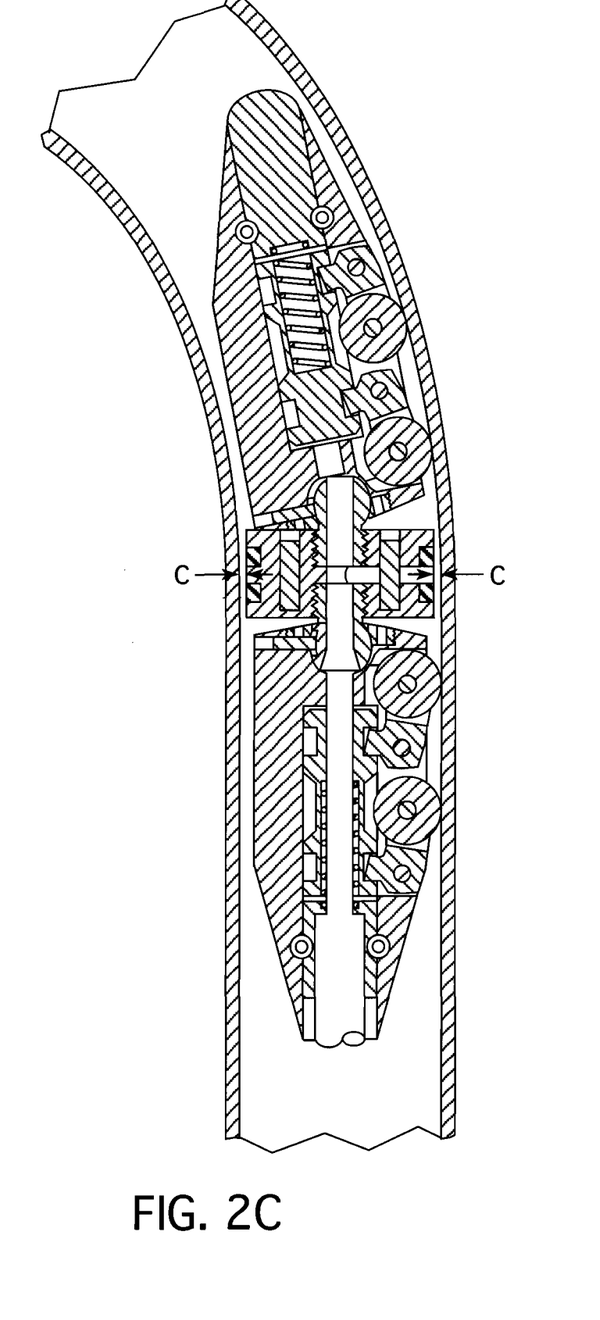
Figure 2D:
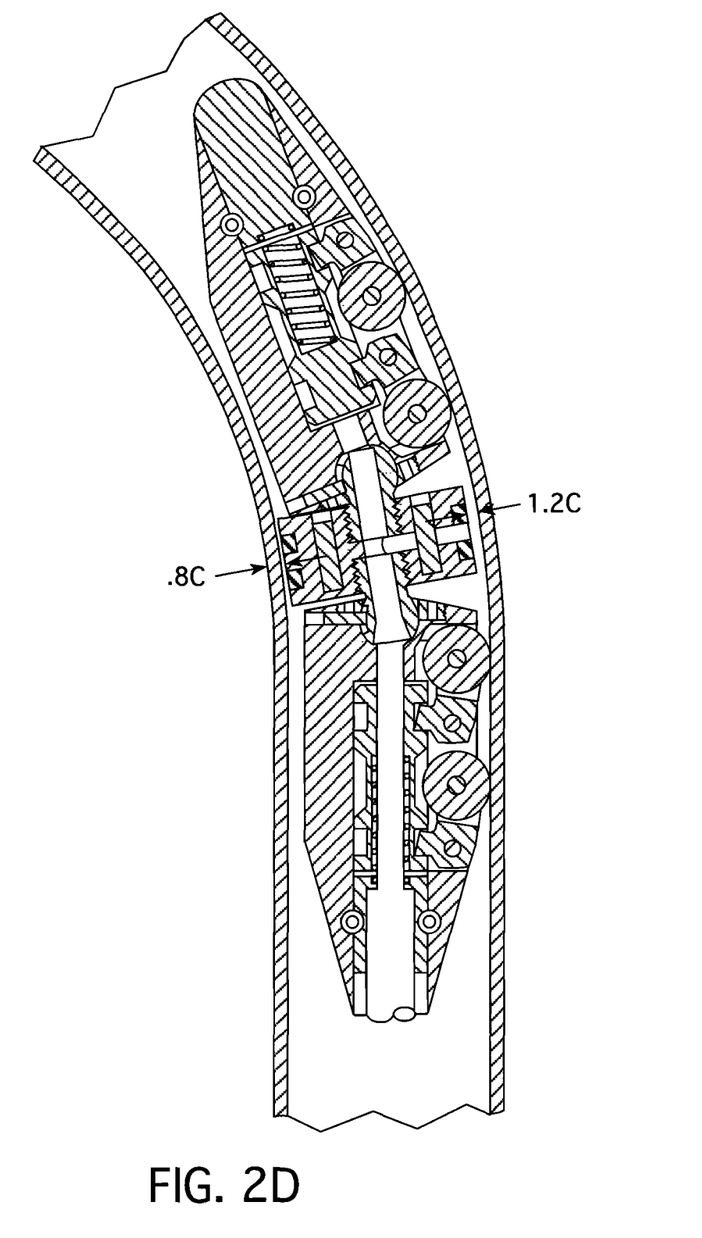
Figure 2E:
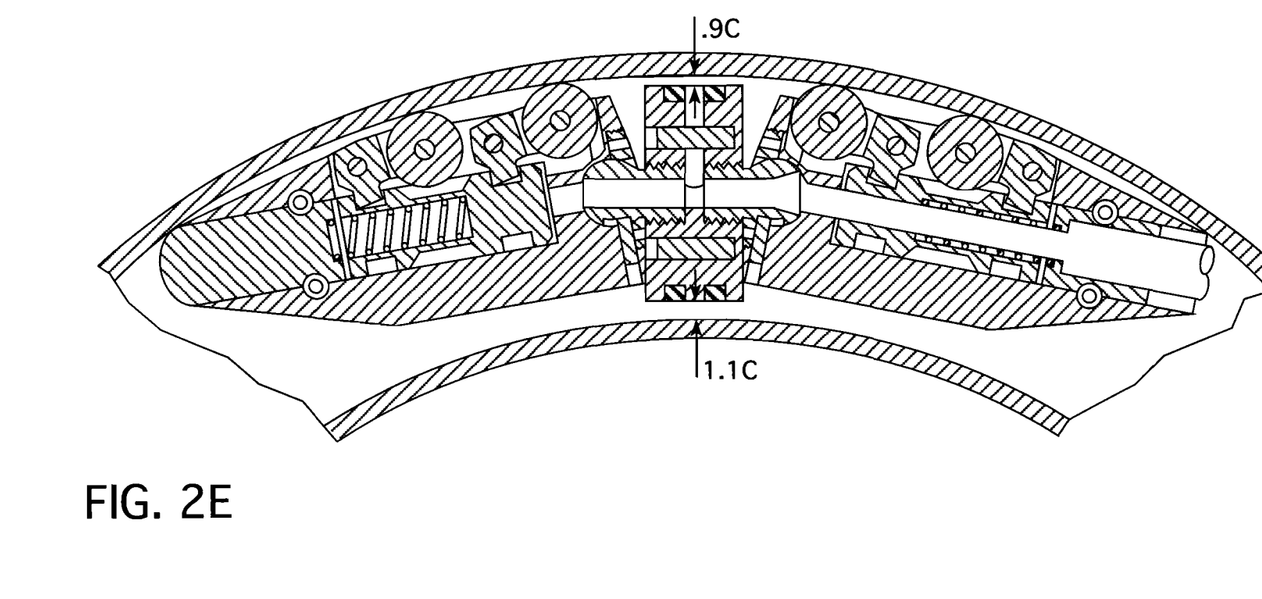

FIGS. 2a through 2e show the centering ability of the eddy current probe 1. The tube 6 in the figures is typically the smallest outside diameter of $11/16^{th}$ inch (1.75 cms.) and the smallest radius of 2.2 inch (5.59 cm.) used in nuclear steam generator U-bends. FIG. 2a shows the probe just prior to entering the tube end. The wheels maintain a symmetrical radial gap "C" between the tube and the probe. The probe geometry permits free passage through the U-bend. FIGS. 2b and 2d show the positions where the probe coils are at the closest radial gap (0.8 c) from the tube surface. While the probe coils are not exactly coincident with the tube center line when passing through sections of the U-bend, this small offset is well within the limits of the probe and an improvement over existing probes. Typically, for other probes used in the industry, the coil diameter must be reduced to permit passage of the probe through the smaller radius U-bends. This reduction in probe diameter decreases the resolution and performance of the probe.

Figure 3:
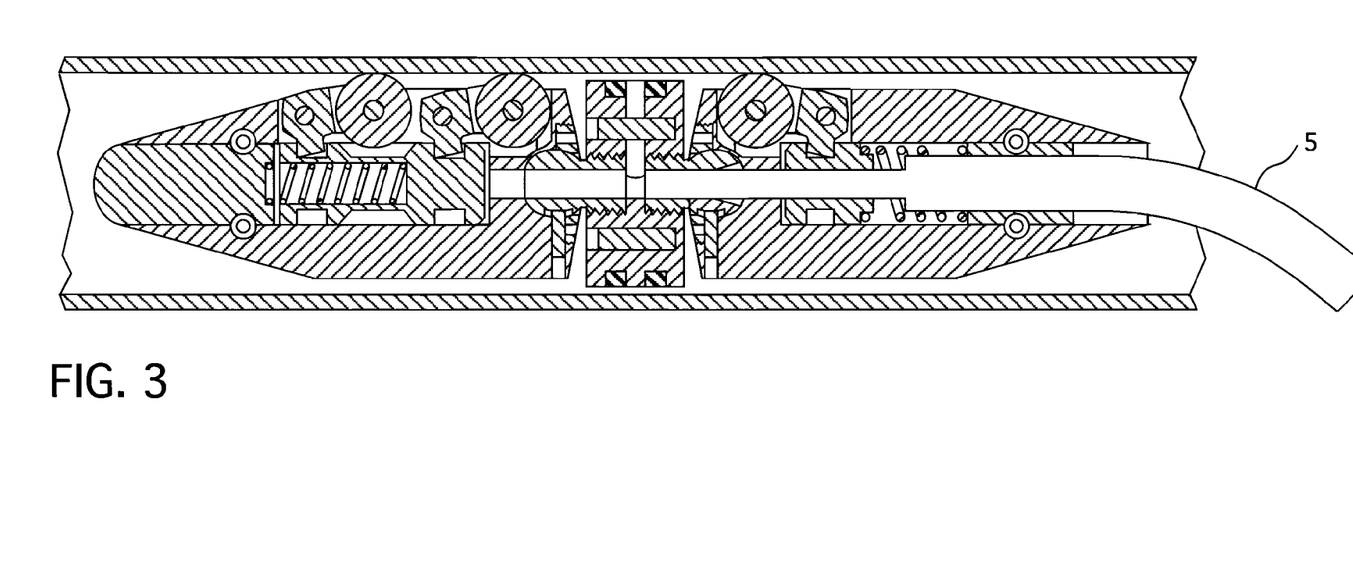
FIG. 3 is a cross sectional view of a second embodiment of the probe of this invention.

FIG. 3 is an optional configuration of the probe with one wheel to each set in the tail. This configuration provides more space for securing the flexible cable 5 with some decrease in the centering ability of the coils.

Figure 4A:
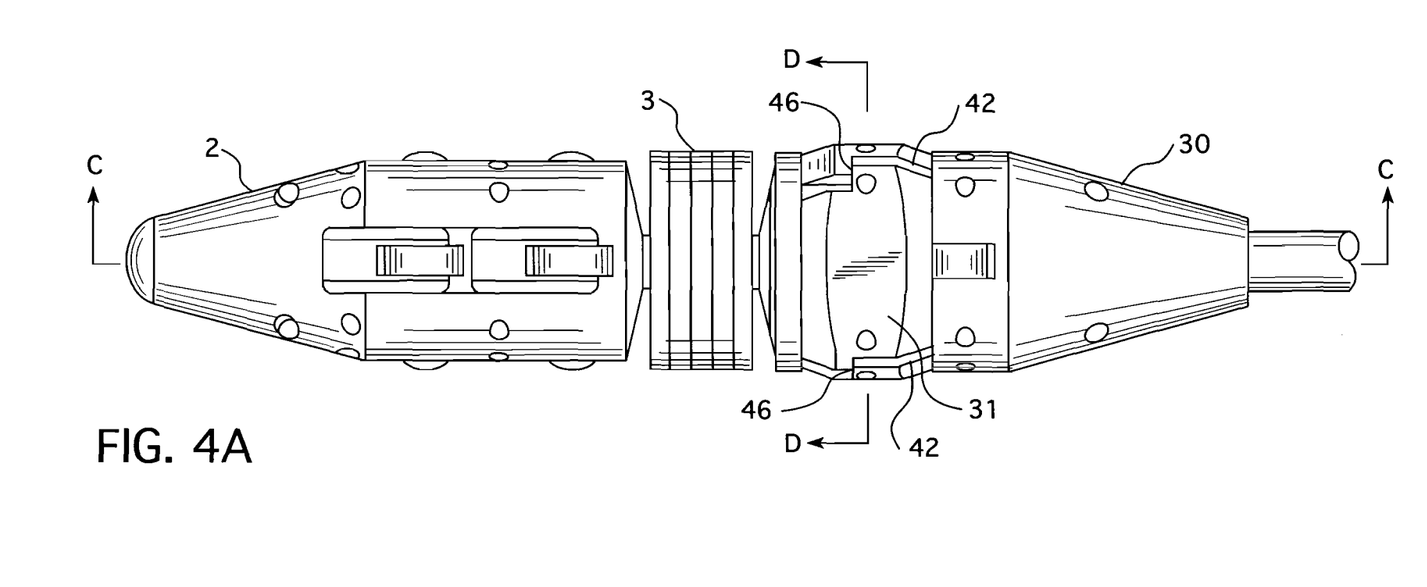
FIG. 4a is a plan view of a third embodiment of this invention.
Figure 4B:
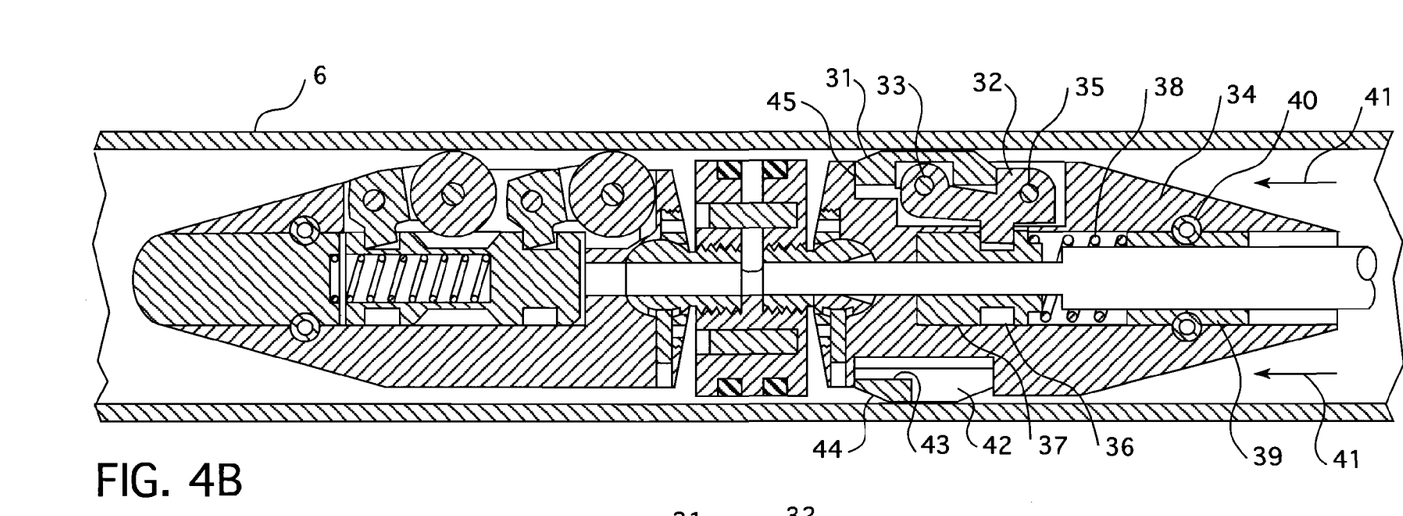
FIG. 4b is a cross sectional view of the probe shown in FIG. 4a taken along the lines C-C thereof, positioned within a section of tubing to be inspected.
Figure 4C:
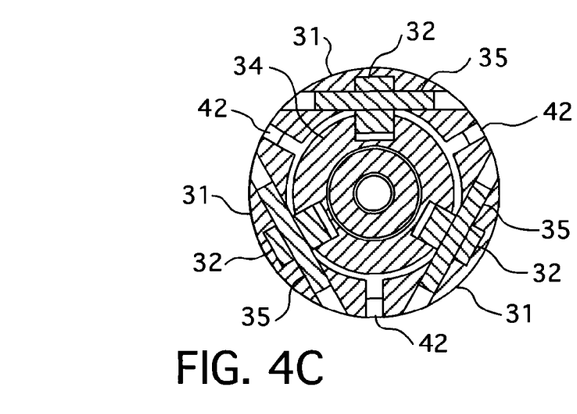
FIG. 4c is a cross sectional view of the embodiments shown in FIG. 4a taken along the lines D-D thereof.

FIGS. 4a, 4b and 4c show an eddy current probe that uses compressed air to aid insertion and reduce or eliminate flexible cable buckling. Nose assembly 2 and coil assembly 3 are the same as used in FIG. 1. The difference is the tail assembly 30. Similar to the wheels used in the nose, there are at least three seal pads 31 that engage sliding contact with the side of the tube 6. Each seal pad is coupled to a cam 32 with axle 33 and is free to pivot on the axis of the axle. The cams are coupled to the tail body 34 and rotate about pins 35. Each cam 32 is engaged into opening 36 of plunger 37. Plunger 37 is free to slide co-linearly along the axis of the tail body 34 and is biased to the left by means of compression spring 38. The reaction force of spring 38 is the sleeve 39 then through spring pins 40 secured to the tail body 34. As can be seen, the radial motion of each seal pad towards the tube 6 is closely coupled by means of cams 32 and plunger 37. Like the wheels in the nose assembly 2, all seal pads 31 travel the same radial distance outward, applying the same pressure keeping the probe 1 centered in the tube 6.

Another advantage is that for varying tube inside diameters, a near constant radial outward force is achieved with the cam/plunger/spring geometry. A relatively larger amount of radial seal pad travel results from only a small amount of plunger travel. Locating the spring axially along the axis of the probe provides more space allowing a relatively small spring displacement per spring length.

While the seal pads 31 keep the probe centered in the tube, the main function is to provide a motive force along the tube axis during probe insertion. A compressed fluid such as air 41 is injected between the tube 6 and the probe tail section 4. Since the seal pads 31 provide a pressure boundary between the probe and the tube, the higher pressure fluid exerts an insertion force (to the left) on the probe. In order to limit leakage past the seal pads, the outward force of seal pads 31 against the inside diameter of the tube 6 increases with increasing fluid pressure. Shown in FIGS. 4a, 4b and 4c are openings 42 which permit compressed air to act on the inner pad radial surface 43. Since the outer pad radial surface 44 is at a lower pressure (open tube) than the compressed air, there is a net outward radial force that is directly proportional to the compressed air pressure. Seal pads 31 will be forced radially outward and move along slidable interface 45. This system creates a dynamic seal. During translation of the probe into the tube, resistance to probe motion will give rise to the air pressure and hence increase seal outward radial force. When the probe is withdrawn from the tube, the applied air pressure can be minimized. At the low air pressure, seal friction and wear will predominantly be from the applied force of the spring 38.

It should also be realized that the overlap 46 between seal pads provides the ability for the seal to function in varying tube inside diameters. While the dynamic seal is shown as part of the probe design with its centering features, the dynamic seal can be used as a standalone addition to enhance the mobility of existing eddy current probe designs. In addition, as previously mentioned, while the probe was shown as a vehicle for translating an eddy current sensor, it can also be used to transport other nondestructive sensors such as cameras, ultrasonic probes, etc.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. An elongated nondestructive sensor inspection probe having a central axis running along the elongated dimension of the probe, for nondestructively examining the walls of tubing comprising:
    a nose section having at least three sets of rollers substantially equidistantly spaced around a circumference of the nose section, the sets of rollers being biased in a radially outward direction to contact an interior wall of the tubing, wherein the nose section includes a plunger reciprocally moveable in the axial direction, a plurality of cams, with at least one of the cams coupled between a corresponding one of the sets of rollers and the plunger, with each cam respectively rotatable about a corresponding pin and means for biasing the plunger in one direction that rotates each cam in a direction to bias the rollers radially outward with substantially equal force;
    a nondestructive sensor section suspended at one axial end from the nose section and coupled to the nose section with a pivot coupling that enables the nondestructive sensor section a limited degree of rotation relative to the nose section; and
    a tail section coupled to the nondestructive sensor section at another axial end with a pivot coupling that enables the nondestructive sensor section a limited degree of rotation relative to the tail section, the tail section having a centering device biased radially outward from a central body of the tail section, the centering device having a plurality of contact points with the interior wall of the tubing with each of the contact points being biased outward around a circumference of the tail section, with substantially equal pressure.

2. The nondestructive sensor inspection probe of claim 1 wherein the plunger is coaxially supported within the nose section.

3. The nondestructive sensor inspection probe of claim 2 wherein the plunger is spring biased.

4. The nondestructive sensor inspection probe of claim 1 wherein the tail section includes a second plunger reciprocally moveable in the axial direction, a second plurality of cams, with at least one of the cams coupled between a corresponding one of the contact points and the second plunger, with each cam respectively rotatable about a corresponding pin and means for biasing the second plunger in a second direction that rotates each second cam in a direction to bias the contacts radially outward with substantially equal force.

5. The nondestructive sensor inspection probe of claim 4 wherein the plunger in the tail section includes an axial passage through which a signal cable extends from the nondestructive sensor section to a rear of the tail section.

6. The nondestructive sensor inspection probe of claim 5 wherein the pivot coupling between the tail section and the nondestructive sensor section includes an axial passage through which the signal cable passes from the nondestructive sensor section to the tail section.

7. The nondestructive sensor inspection probe of claim 6 wherein the axial passage through the pivot coupling between the tail section and the nondestructive sensor section has a widened tapered exit into the tail section.

8. The nondestructive sensor inspection probe of claim 1 wherein the contact points are rollers that are substantially equidistantly spaced around a circumference of the tail section.

9. The nondestructive sensor inspection probe of claim 1 wherein the contact points are separate, discontinuous sections of an annular circumferential seal that extend around and project outward from a central body of the tail section and are biased against the interior wall of the tubing.

10. The nondestructive sensor inspection probe of claim 1 wherein the nondestructive sensor section is supported substantially equidistantly spaced around a circumference of the nondestructive sensor section from the pipe wall as the nondestructive sensor inspection probe traverses a bend in the piping.

11. The nondestructive sensor inspection probe of claim 10 wherein the equidistant spacing around the circumference of the nondestructive sensor section from the interior wall of the pipe does not vary substantially more than from +20% to −20% of the nominal spacing.

12. The nondestructive sensor inspection probe of claim 1 wherein each set of rollers includes two rollers that move radially together.

13. The nondestructive sensor inspection probe of claim 1 including a stop for limiting the degree of rotation of the pivot coupling between the nondestructive sensor section and the tail section.

14. The nondestructive sensor inspection probe of claim 13 wherein the stop for limiting the degree of rotation of the pivot coupling between the nondestructive sensor section and the tail section prevents axial rotation of the tail section relative to the nondestructive sensor section.

15. An elongated nondestructive sensor inspection probe having a central axis running along the elongated dimension of the probe, for nondestructively examining the walls of tubing comprising:
    a nose section having at least three sets of rollers substantially equidistantly spaced around a circumference of the nose section, the sets of rollers being biased in a radially outward direction to contact an interior wall of the tubing with a substantially equally applied force biasing each of the sets of rollers;
    a nondestructive sensor section suspended at one axial end from the nose section and coupled to the nose section with a pivot coupling that enables the nondestructive sensor section a limited degree of rotation relative to the nose section; and
    a tail section coupled to the nondestructive sensor section at another axial end with a pivot coupling that enables the nondestructive sensor section a limited degree of rotation relative to the tail section, the tail section having a centering device biased radially outward from a central body of the tail section, the centering device having a plurality of contact points with the interior wall of the tubing with each of the contact points being biased outward around a circumference of the tail section, with substantially equal pressure, wherein the contact points are sections of an annular circumferential seal that extend around and project outward from a central body of the tail section and are biased against the interior wall of the tubing and the sections of the annular circumferential seal overlap circumferentially to accommodate varying diameters of the tubing.

16. An elongated nondestructive sensor inspection probe having a central axis running along the elongated dimension of the probe, for nondestructively examining the walls of tubing comprising:

a nose section having at least three sets of rollers substantially equidistantly spaced around a circumference of the nose section, the sets of rollers being biased in a radially outward direction to contact an interior wall of the tubing with a substantially equally applied force biasing each of the sets of rollers;

a nondestructive sensor section suspended at one axial end from the nose section and coupled to the nose section with a pivot coupling that enables the nondestructive sensor section a limited degree of rotation relative to the nose section; and a tail section coupled to the nondestructive sensor section at another axial end with a pivot coupling that enables the nondestructive sensor section a limited degree of rotation relative to the tail section, the tail section having a centering device biased radially outward from a central body of the tail section, the centering device having a plurality of contact points with the interior wall of the tubing with each of the contact points being biased outward around a circumference of the tail section, with substantially equal pressure, wherein the contact points are sections of an annular circumferential seal that extend around and project outward from a central body of the tail section and are biased against the interior wall of the tubing and the sections of the annular circumferential seal each include a fluid path extending from a rear of the tail section to a radially facing interior surface of the sections of the annular circumferential seal so that a pressure build up to the rear of the tail section forces the seal in a radially outward direction.

17. A nondestructive tube inspection probe for examining the condition of a wall of a tube from an interior thereof, the probe comprising:

a probe body having an axis extending along a direction of travel through the tube; and a centering seal extending around an entire circumference of the probe body and biased radially outward from the probe body, the centering seal having a plurality of circumferential, separate segments that, respectively, only partially extend around the circumference of the probe body and make contact with an inside of the wall of the tube to be inspected with each of the segments being biased outward around a circumference of the probe body by a force in which the force is separately applied to each of the segments, with the same pressure, applied from an axially reciprocal plunger which is connected to each of the segments.

18. The nondestructive sensor tube inspection probe of claim 17 wherein the circumferential segments overlap circumferentially to accommodate varying diameters of the tubing.

19. The nondestructive sensor tube inspection probe of claim 17 wherein the circumferential segments each include a fluid path extending from a rear of the probe to a radially facing interior surface of the segments of the circumferential seal so that a pressure build up to the rear of the probe body forces the seal in a radially outward direction.

* * * * *